United States Patent [19]

Schneider et al.

[11] Patent Number: 4,636,510

[45] Date of Patent: Jan. 13, 1987

[54] 4-PHENYL-TETRAHYDRO-FURANO-PYRIDINES AND ANTI-DEPRESSANT PHARMACEUTICAL COMPOSITIONS CONTAINING SAME

[75] Inventors: Claus Schneider, Ingelheim am Rhein; Gerhard Walther, Bingen; Karl-Heinz Weber, Gau-Algesheim; Wolf D. Bechtel, Appenheim; Karin Böke-Kuhn, Gau-Algesheim, all of Fed. Rep. of Germany

[73] Assignee: Boehringer Ingelheim KG, Ingelheim am Rhein, Fed. Rep. of Germany

[21] Appl. No.: 601,910

[22] Filed: Apr. 19, 1984

[30] Foreign Application Priority Data

Apr. 27, 1983 [DE] Fed. Rep. of Germany ....... 3315157

[51] Int. Cl.⁴ .................. A61K 31/44; C07D 491/048
[52] U.S. Cl. .................................... 514/302; 546/115; 546/116
[58] Field of Search ............... 546/115, 116; 424/256; 514/302

[56] References Cited

U.S. PATENT DOCUMENTS 4,104,390 8/1978 Ferrand et al. .................... 424/256
4,282,227 8/1981 Brenner ............................. 424/256
4,322,423 3/1982 Schneider et al. ................. 424/256

OTHER PUBLICATIONS

Herz et al., J.A.C.S. vol. 77, pp. 3554–3556 (1955).

Primary Examiner—Henry R. Jiles
Assistant Examiner—Bernard I. Dentz
Attorney, Agent, or Firm—Hammond & Littell, Weissenberger & Dippert

[57] ABSTRACT

The invention relates to 4-phenyl-tetrahydro-furano-pyridines of the formulas

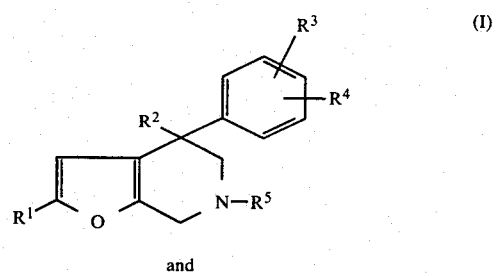

and

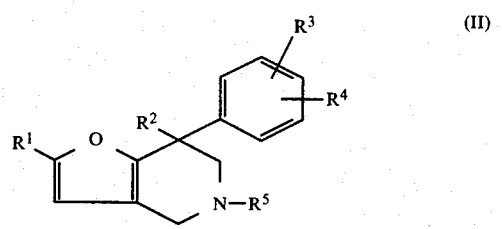

wherein $R^1$ to $R^5$ are variously defined. The compounds of the invention are intended to be used as anti-depressants with, in particular, thymoleptic and central-stimulant properties.

10 Claims, No Drawings

4-PHENYL-TETRAHYDRO-FURANO-PYRIDINES AND ANTI-DEPRESSANT PHARMACEUTICAL COMPOSITIONS CONTAINING SAME

The invention relates to novel 4-phenyl-tetrahydro-furano-pyridines, processes for the preparation thereof, and pharmaceutical compositions containing them. More specifically, the invention relates to compounds of the formulas

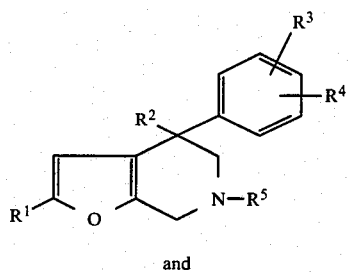
(I)

and

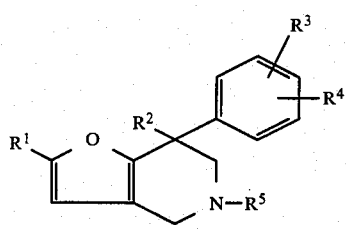
(II)

wherein
$R^1$ represents hydrogen, fluorine, chlorine, bromine, an alkyl group having from 1 to 4 carbon atoms, a hydroxyalkyl group having 1 or 2 carbon atoms, an alkoxyalkyl group wherein each alkyl group may have 1 or 2 carbon atoms, a pyrrolidinomethyl group, or a dialkylaminomethyl group wherein each alkyl group may have 1 or 2 carbon atoms;
$R^2$ represents hydrogen, hydroxyl, methoxy, or ethoxy;
$R^3$ and $R^4$, which may be the same or different, each represent hydrogen, fluorine, chlorine, bromine, methyl, ethyl, hydroxyl, methoxy, acetoxy, or benzyloxy or $R^3$ and $R^4$ together with the phenyl ring form a 3,4-benzodioxanyl group; and
$R^5$ represents hydrogen, an alkyl group having from 1 to 4 carbon atoms, or a benzyl or o-chlorobenzyl group,
with the proviso that in Formula II $R^2$ represents hydrogen and $R^1$ does not represent hydroxyalkyl. The invention also relates to the pharmacologically acceptable acid addition salts of the above-mentioned compounds of Formulas I and II.

The novel compounds may be prepared by various methods. Compounds of Formula I may be obtained, for example, by reacting a 4,5,6,7-tetrahydro-4-hydroxy-furano[2,3-c]pyridine of the formula

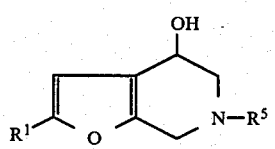
(III)

wherein $R^1$ and $R^5$ are as hereinbefore defined, with a benzene derivative of the formula

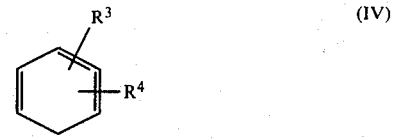
(IV)

wherein $R^3$ and $R^4$ are as hereinbefore defined.

Dependent upon the type of benzene derivative used, the reaction is carried out using acid catalysts such as methanesulfonic acid or aluminum chloride at ambient temperature or with cooling. If a compound of Formula IV contains only one substituent, both the o-isomer and also the p-isomer will be obtained in this reaction, and these may be separated by chromatography. With use of this procedure, compounds of Formula I wherein $R^2$ represents hydrogen are obtained.

To prepare compounds of Formula I wherein $R^2$ represents a hydroxyl group, a compound of Formula III is converted into the corresponding 4-oxo compound by means of a ketone such as acetone or cyclohexanone and an aluminum alkoxide under the conditions of Oppenauer oxidation. The starting product of Formula III is appropriately dissolved in an inert organic solvent such as toluene, benzene, xylene, etc., and refluxed with the addition of the ketone and the aluminum alkoxide. The resulting 4-oxo compound of the formula

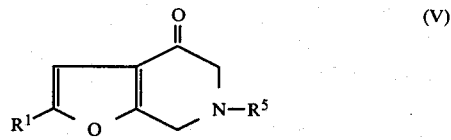
(V)

wherein $R^1$ and $R^5$ are as hereinbefore defined, is then reacted, with cooling, with a solution of a corresponding phenylmagnesium bromide of the formula

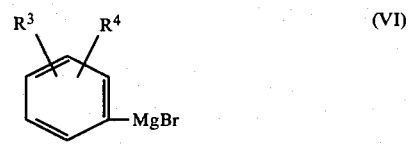
(VI)

wherein $R^3$ and $R^4$ are as hereinbefore defined.

Compounds of Formula II are obtained, starting from a corresponding 2-furfurylamino-1-phenyl-ethanol of the formula

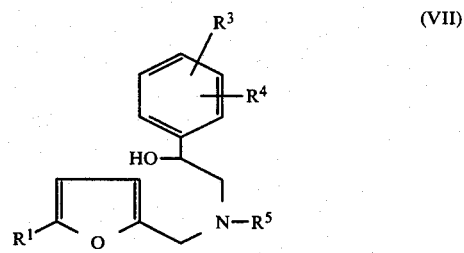
(VII)

wherein the groups $R^1$, $R^3$, $R^4$, and $R^5$ have the meanings given hereinbefore for the compounds of Formula II, by condensation with trifluoroacetic acid or trifluoromethane sulfonic acid. The starting product of Formula VII is dissolved in an inert organic solvent, e.g., ethylene chloride, and refluxed with the acid.

If $R^5$ represents a benzyl or o-chlorobenzyl group, such an end product can be debenzylated by conventional methods, preferably catalytically, with palladium/charcoal. It is also possible to introduce a halogen atom, a dialkylamino group or a pyrrolidinomethyl group into a compound of Formula I wherein $R^1$ represents hydrogen. For this purpose, the compound wherein $R^1$=hydrogen is dissolved in an inert organic solvent, e.g., acetonitrile, and heated for some time with dialkylamine and formaldehyde or a halogenation agent.

In the case of a compound of Formula I wherein $R^2$ represents a hydroxyl group, this group may be split off in the following way:

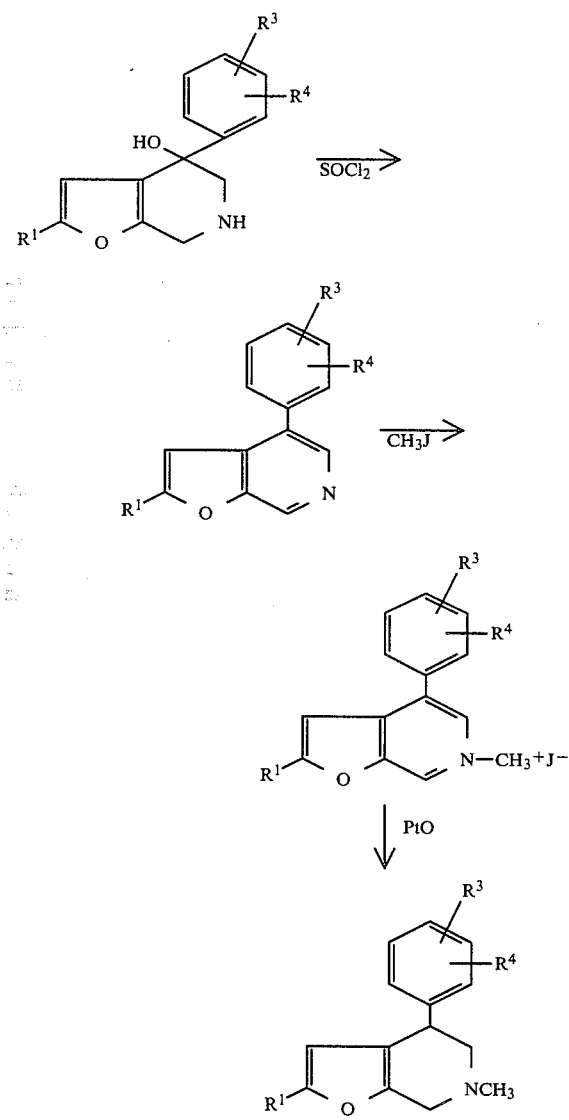

To prepare compounds wherein $R^1$ is hydroxyalkyl, it is advisable to use a starting compound of Formula III or IV which has an alkoxycarbonyl group in the 2-position. After the benzene ring has been condensed on in the 4-position, the alkoxycarbonyl group is then converted, optionally, into the corresponding hydroxyalkyl group, preferably with lithium alanate in an inert organic solvent such as tetrahydrofuran at ambient temperature.

If one or both of the groups $R^3$ and $R^4$ represents a hydroxyl group, these may be converted in known manner, e.g., by reaction with boron trifluoride/methanol, into a methoxy group or, for example, by heating with acetic anhydride, into an acetoxy group.

By use of procedures such as are described above, the following compounds, possibly in the form of their acid addition salts, may, for example, be obtained:

(a) 2,6-dimethyl-4-hydroxy-4-(p-bromophenyl)-4,5,6,7-tetrahydro-furano[2,3-c]pyridine (b) 4-hydroxy-4-(p-bromophenyl)-6-methyl-4,5,6,7-tetrahydro-furano[2,3-c]pyridine (c) 4-methoxy-4-(p-bromophenyl)-6-methyl-4,5,6,7-tetrahydro-furano[2,3-c]pyridine (d) 2-hydroxymethyl-4-hydroxy-4-(p-tolyl)-4,5,6,7-tetrahydro-furano[2,3-c]pyridine (e) 2,6-dimethyl-4-hydroxy-4-(m-methoxyphenyl)-4,5,6,7-tetrahydro-furano[2,3-c]pyridine (f) 2,6-dimethyl-4-hydroxy-4-(p-tolyl)-4,5,6,7-tetrahydro-furano[2,3-c]pyridine (g) 2,6-dimethyl-4-hydroxy-4-(p-ethylphenyl)-4,5,6,7-tetrahydro-furano[2,3-c]pyridine (h) 2,6-dimethyl-4-hydroxy-4-(p-chlorophenyl)-4,5,6,7-tetrahydro-furano[2,3-c]pyridine (i) 4-(p-tolyl)-6-methyl-4,5,6,7-tetrahydro-furano[2,3-c]pyridine (j) 2,6-dimethyl-4-(3,4-dihydroxyphenyl)-4,5,6,7-tetrahydro-furano[2,3-c]pyridine (k) 2-hydroxymethyl-4-(p-tolyl)-6-methyl-4,5,6,7-tetrahydro-furano[2,3-c]pyridine (l) 4-(p-hydroxyphenyl)-6-methyl-4,5,6,7-tetrahydro-furano[2,3-c]pyridine (m) 4-(o-hydroxyphenyl)-4,5,6,7-tetrahydro-furano[2,3-c]pyridine (n) 2,6-dimethyl-4-(p-hydroxyphenyl)-4,5,6,7-tetrahydro-furano[2,3-c]pyridine (o) 2,6-dimethyl-4-(o-hydroxyphenyl)-4,5,6,7-tetrahydro-furano[2,3-c]pyridine (p) 2,6-dimethyl-4-(p-acetoxyphenyl)-4,5,6,7-tetrahydro-furano[2,3-c]pyridine (q) 2,6-dimethyl-4-(p-bromophenyl)-4,5,6,7-tetrahydro-furano[2,3-c]pyridine (r) 2,6-dimethyl-4-(o-bromophenyl)-4,5,6,7-tetrahydro-furano[2,3-c]pyridine (s) 2-methyl-4-(p-methoxyphenyl)-4,5,6,7-tetrahydro-furano[2,3-c]pyridine (t) 4-(3,4-dihydroxyphenyl)-6-methyl-4,5,6,7-tetrahydro-furano[2,3-c]pyridine (u) 4-(p-methoxyphenyl)-6-methyl-4,5,6,7-tetrahydro-furano[2,3-c]pyridine (v) 4-(o-methoxyphenyl)-6-methyl-4,5,6,7-tetrahydro-furano[2,3-c]pyridine (w) 2,6-dimethyl-4-(p-chlorophenyl)-4,5,6,7-tetrahydro-furano[2,3-c]pyridine (x) 2,6-dimethyl-4-(o-chlorophenyl)-4,5,6,7-tetrahydro-furano[2,3-c]pyridine (y) 2,6-dimethyl-4-(p-fluorophenyl)-4,5,6,7-tetrahydro-furano[2,3-c]pyridine (z) 2,6-dimethyl-4-(o-fluorophenyl)-4,5,6,7-tetrahydro-furano[2,3-c]pyridine (aa) 2-methyl-4-(p-bromophenyl)-4,5,6,7-tetrahydro-furano[2,3-c]pyridine (bb) 2-methyl-4-(o-bromophenyl)-4,5,6,7-tetrahydro-furano[2,3-c]pyridine (cc) 2-methyl-4-phenyl-4,5,6,7-tetrahydro-furano[2,3-c]pyridine (dd) 2-pyrrolidinomethyl-4-(p-methoxyphenyl)-6-methyl-4,5,6,7-tetrahydro-furano[2,3-c]pyridine
(ee) 2-methyl-4-phenyl-6-ethyl-4,5,6,7-tetrahydro-furano[2,3-c]pyridine
(ff) 2-methyl-4-phenyl-6-n-propyl-4,5,6,7-tetrahydro-furano[2,3-c]pyridine
(gg) 4-(p-fluorophenyl)-4,5,6,7-tetrahydro-furano[2,3-c]pyridine
(hh) 4-(3,4-dihydroxyphenyl)-4,5,6,7-tetrahydro-furano[2,3-c]pyridine
(ii) 2-methyl-4-(3,4-dihydroxyphenyl)-4,5,6,7-tetrahydro-furano[2,3-c]pyridine
(jj) 2-methyl-4-phenyl-6-n-butyl-4,5,6,7-tetrahydro-furano[2,3-c]pyridine
(kk) 2-methyl-4-(1,4-benzodioxanyl)-4,5,6,7-tetrahydro-furano[2,3-c]pyridine
(ll) 4-phenyl-6-methyl-4,5,6,7-tetrahydro-furano[2,3-c]pyridine
(mm) 2-ethyl-4-(3,4-dihydroxyphenyl)-6-methyl-4,5,6,7-tetrahydro-furano[2,3-c]pyridine.

Furthermore, the following compounds of Formula II were obtained:
(a) 2,6-dimethyl-4-phenyl-4,5,6,7-tetrahydro-furano[3,2-c]pyridine
(b) 4-phenyl-4,5,6,7-tetrahydro-furano[3,2-c]pyridine
(c) 4-(p-tolyl)-6-methyl-4,5,6,7-tetrahydro-furano[3,2-c]pyridine
(d) 4-phenyl-6-methyl-4,5,6,7-tetrahydro-furano[3,2-c]pyridine
(e) 4-(p-bromophenyl)-6-methyl-4,5,6,7-tetrahydro-furano[3,2-c]pyridine
(f) 4-(p-fluorophenyl)-6-methyl-4,5,6,7-tetrahydro-furano[3,2-c]pyridine
(g) 4-(p-chlorophenyl)-6-methyl-4,5,6,7-tetrahydro-furano[3,2-c]pyridine
(h) 2,6-dimethyl-4-(p-fluorophenyl)-4,5,6,7-tetrahydro-furano[3,2-c]pyridine
(i) 4-(p-methoxyphenyl)-6-methyl-4,5,6,7-tetrahydro-furano[3,2-c]pyridine
(j) 2,6-dimethyl-4-(p-tolyl)-4,5,6,7-tetrahydro-furano[3,2-c]pyridine
(k) 2,6-dimethyl-4-(p-chlorophenyl)-4,5,6,7-tetrahydro-furano[3,2-c]pyridine
(l) 2,6-dimethyl-4-(p-bromophenyl)-4,5,6,7-tetrahydro-furano[3,2-c]pyridine
(m) 2,6-dimethyl-4-(p-methoxyphenyl)-4,5,6,7-tetrahydro-furano[3,2-c]pyridine
(n) 2-ethyl-4-(p-fluorophenyl)-6-methyl-4,5,6,7-tetrahydro-furano[3,2-c]pyridine
(o) 2-methyl-4-phenyl-4,5,6,7-tetrahydro-furano[3,2-c]pyridine
(p) 4-(3,4-dihydroxyphenyl)-6-methyl-4,5,6,7-tetrahydro-furano[3,2-c]pyridine
(q) 4-(3-hydroxyphenyl)-6-methyl-4,5,6,7-tetrahydro-furano[3,2-c]pyridine
(r) 4-(3,4-dihydroxyphenyl)-4,5,6,7-tetrahydro-furano[3,2-c]pyridine
(s) 2-bromo-4-(p-fluorophenyl)-6-methyl-4,5,6,7-tetrahydro-furano[3,2-c]pyridine.

The starting compounds of Formulas III and VII can be obtained by methods known per se: Compounds of Formula III can be prepared by condensation of a furfurylglycine ester with ethyl chloroformate, reduction of the resulting 4,5,6,7-tetrahydro-4-oxo-6-ethoxy-carbonyl-furano[2,3-c]pyridine with lithium alanate or sodium borohydride, and splitting off of the ethoxycarbonyl group with an alkali. Starting substances of Formula VII may be obtained, for example, by reacting furfurylmethylamine with p-methyl-phenacylbromide and then with sodium borohydride.

If desired, the compounds of Formula I may be converted into their pharmacologically acceptable acid addition salts by conventional methods. Suitable acids for this include both inorganic acids, such as hydrohalic acids and sulfuric, phosphoric, and aminosulfonic acid and also organic acids, such as formic, acetic, propionic, lactic, glycolic, gluconic, maleic, succinic, tartaric, benzoic, salicylic, citric, ascorbic, oxalic, p-toluenesulfonic, and oxyethanesulfonic acid.

The new compounds of Formulas I and II and the acid addition salts thereof are valuable pharmaceutical substances. In some specific tests, they were found to have powerful anti-depressant properties, particularly a thymoleptic and central-stimulant effect.

One test for determining the anti-depressant activity is tetrabenzine antagonism, the reversal of the ptosis caused by tetrabenazine. The test is carried out on mice, using five animals for each dose. One hour after the test substance is administered, the animals are given 40 mg/kg of tetrabenazine. The ptosis is assessed 75 to 120 minutes after the administration of the tetrabenazine, in accordance with the method described by B. Rubin, M. H. Malone et al., *J. Pharmacol. Exp. Ther.* 120, 125–136 (1957).

In another, biochemical test the starting premise is the fact that in various forms of depression a shortage of biogenic amines, particularly noradrenalin, occurs in certain areas of the brain; the biogenic amines can be increased by preventing the uptake into the neurones. A suitable test arrangement shows that the new compounds particularly inhibit the reabsorption of noradrenalin into the neurones. The test is carried out on homogenized isolated rat's cerebrum, as described by A. S. Horn, *Mol. Pharmacol.* 1971, pages 66–80. The synaptosomes thus obtained are incubated with tritiated noradrenalin and various concentrations of a solution of the test substance in water for ten minutes at 37° C. After incubation has ended, the medium is separated off by filtration, and the radioactivity of the synaptosomes is measured.

A control test without the test substance is carried out simultaneously to determine the quantity of uptake of radioactive amines. The $IC_{50}$ is the quantity of test substance in mol which is sufficient to prevent 50% of the uptake.

Recently, measurement of the $\alpha_2$-receptor antagonism has become increasingly important. The presynaptic $\alpha_2$-receptor, also known as the autoreceptor, regulates the release of noradrenalin which occurs in uncontrolled manner if there is a blockade of the receptor. A prerequisite for the blockage of the receptor is a high affinity of the test substance with the $\alpha_2$-receptor (see, Greenberg et al., *Life Science*, Volume 19, page 69 (1976)).

In the testing described above, it was found that some of the compounds according to the invention have a powerful activity in the tetrabenazine test, whereas others have proven superior to known anti-depressants, for example, in the inhibition of noradrenalin or in the $\alpha_2$-receptor bonding test.

The compounds which can be obtained according to the invention may be used alone, in conjunction with other active substances according to the invention, for example, in mixtures of from 2 to 6 compounds according to the invention, or possible together with other pharmacologically active substances. Suitable forms for administration include, for example, tablets, capsules, suppositories, solutions, syrups, emulsions, or dispersible powders. Corresponding tablets may be produced, for example, by mixing the active substance or substances with known excipients, for example, inert diluents such as calcium carbonate, calcium phosphate, or lactose, disintegrants such as corn starch or alginic acid, binders such as starch or gelatine, lubricants such as magnesium stearate or talc, and/or agents for obtaining sustained release, such as carboxypolymethylene, carboxymethylcellulose, cellulose acetate phthalate, or polyvinyl acetate. The tablets may also consist of several layers.

Coated tablets may be prepared in analogous fashion by covering tablet cores, produced in the same way as the tablets, with substances conventionally used for tablet coatings, e.g., collidone or shellac, gum arabic, talc, titanium dioxide, or sugar. To obtain delayed release or avoid incompatibilities, the core may also consist of several layers. Similarly, the coating may also consist of several layers in order to obtain delayed release, while the excipients used for the tablets may be used in the coating also.

Syrups containing the active substances of combinations of active substances according to the invention may additionally contain a sweetener such as saccharin, cyclamate, glycerol, or sugar and a flavor-improving agent, e.g., a flavoring such as vanillin or orange extract. They may also contain suspension adjuvants or thickeners such as sodium carboxymethylcellulose, wetting agents, e.g., condensation products of fatty alcohols with ethylene oxide, or preservatives such as p-hydroxybenzoates.

Injection solutions are prepared in conventional manner, e.g., by adding preservatives such as p-hydroxybenzoates or stabilizers such as alkali metal salts of ethylenediaminetetraacetic acid, and these are then transferred into injection vials or ampules.

Capsules containing one or more active substances or combinations thereof may, for example, be prepared by mixing the active substances with inert carriers such as lactose or sorbitol and encapsulating them in gelatin capsules.

Suitable suppositories may be produced, for example, by mixing with carriers provided for this purpose. Examples of such carriers include neutral fats or polyethyleneglycol or derivatives thereof.

The excellent activity of the pharmacologically active compounds of Formula I and II and of their pharmacologically, i.e., biologically, acceptable acid addition salts makes it possible to use them as anti-depressants for the treatment of individuals needing such treatment. For such treatment, the compounds of Formula I and II and their pharmacologically acceptable salts can be incorporated, optionally in combination with other active ingredients, in manner known per se, into the usual pharmaceutical preparpations or forms of administration described above. The daily dose for adults is from about 0.75 to 375 mg (from about 0.01 to 5 mg/kg), preferably from about 1.5 to 188 mg (from about 0.02 to 2.5 mg/kg), more particularly, from about 3.75 to 75.0 mg (from about 0.05 to 1.0 mg/kg), generally administered in the form of several, preferably from 1 to 3, individual doses to achieve the desired results. Dependent upon the type and body weight of the patient to be treated, on the type and severity of the disease, on the type of preparation and on the route of administration as well as on the period or interval over which the administration takes place, it may, however, be necessary to deviate from the above dosages. Thus, it may be sufficient in some cases to administer more or less than the above-mentioned amounts of active ingredients. The optimum dosage and route of administration of the active ingredients which are necessary in each case can easily be determined by one skilled in the art.

The following examples are intended to illustrate the invention and should not be construed as limiting the invention thereto.

EXAMPLES

Example 1

4-(p-Methoxyphenyl)-6-methyl-4,5,6,7-tetrahydro-furano[2,3-c]pyridine

A quantity of 14.5 gm (0.095 mol) of 4-hydroxy-6-methyl-4,5,6,7-tetrahydro-furano[2,3-c]pyridine was added to 30 gm of anisole in 90 gm of methanesulfonic acid, and the mixture was stirred for one hour at 5° to 10° C. The reaction mixture was poured onto ice and neutralized with aqueous ammonia solution. It was extracted with ether, the ether solution was dried, and the solvent was distilled off. The residue was purified over silica gel [cyclohexane/ethyl acetate (1:1)] and separated off. After the solvent was removed, the residue of the first fraction was mixed with ethereal hydrochloric acid. The hydrochloride of the title compound crystallized out.

Yield: 11.0 gm (40.8% of theory)

M.p.: 199°–200° C.

The second fraction contained the 4-(o-methoxyphenyl)-6-methyl-4,5,6,7-tetrahydro-furano[2,3-c]pyridine which crystallized after the solvent was distilled off.

Yield: 1.6 gm

M.p.: 116°–117° C.

By use of procedures analogous to that described above, the following compounds were prepared: Starting from 4-hydroxy-6-methyl-4,5,6,7-tetrahydro-furano[2,3-c]pyridine:
(i) 4-(p-hydroxyphenyl)-6-methyl-4,5,6,7-tetrahydro-furano[2,3-c]pyridine (m.p.: 210°–211° C.)
(ii) 4-(3,4-dihydroxyphenyl)-4,5,6,7-tetrahydro-furano[2,3-c]pyridine (hydrochloride m.p.: 262°–263° C.)

Starting from 2,6-dimethyl-4-hydroxy-4,5,6,7-tetrahydro-furano[2,3-c]pyridine:
(iii) 2,6-dimethyl-4-(3,4-dihydroxyphenyl)-4,5,6,7-tetrahydro-furano[2,3-c]pyridine (hydrochloride m.p.: 237°–238° C.)
(iv) 2,6-dimethyl-4-p-hydroxyphenyl)-4,5,6,7-tetrahydro-furano[2,3-c]pyridine (hydrochloride m.p.: 222°–223° C.)
(v) 2,6-dimethyl-4-(o-hydroxyphenyl)-4,5,6,7-tetrahydro-furano[2,3-c]pyridine (hydrochloride m.p.: 259°–260° C.)

The starting compound 4-hydroxy-6-methyl-4,5,6,7-tetrahydro-furano[2,3-c]pyridine was obtained as follows:

(a)

4-Oxo-6-ethoxycarbonyl-4,5,6,7-tetrahydro-furano[2,3-c]pyridine

One hundred seventy-nine grams (1.65 mol) of ethyl chloroformate were added dropwise, under cooling with ice, to 274.5 gm (1.5 mol) of N-furfurylglycine ester and 167 gm of triethylamine in 2000 ml of methylene chloride. The reaction mixture was stirred for a further hour at ambient temperature and then extracted with 500 ml of dilute hydrochloric acid. The organic phase was separated off, dried, and concentrated. The compound obtained was heated to 50° C. for one hour with 1.5 mol of potassium hydroxide in 200 ml of methanol. The reaction mixture was concentrated until it crystallized. The crystals were recovered by suction filtration and dissolved in a small amount of water. After addition of semi-concentrated hydrochloric acid, an oil separated out and was extracted with methylene chloride. After drying and removal of the solvent, the residue was mixed with 69 ml of thionyl chloride and refluxed for six hours. All volatile constituents were eliminated in vacuo.

The residue was dissolved in 2000 ml of ethylene chloride and mixed with 3 mol of aluminum chloride. After one minute, the reaction mixture was poured onto ice. The organic constituents were extracted with methylene chloride. The mixture was then dried and concentrated. The residue was combined with dilute ammonia, the solution was extracted with ether and dried, and the ether was distilled off. The title compound, which crystallized out from a mixture of diisopropylether and cyclohexane, had a melting point of 63°–64° C.

(b)
4-Hydroxy-6-methyl-4,5,6,7-tetrahydro-furano[2,3-c]pyridine

A quantity of 52.3 gm (0.25 mol) of 4-oxo-6-ethoxycarbonyl-4,5,6,7-tetrahydro-furano[2,3-c]pyridine was dissolved in 13 gm of lithium alanate in 300 ml of absolute tetrahydrofuran and then added dropwise to 300 ml of absolute tetrahydrofuran at 10°–15° C., under cooling with ice. After it had all been added, the mixture was refluxed for 30 minutes. After cooling, the excess lithium alanate was destroyed with an aqueous tetrahydrofuran solution [THF/H$_2$O (90:10)]. Thirteen hundred milliliters of 40% diammonium tartrate solution were added to the reaction mixture, and the organic phase was separated off and dried. After the solvent was eliminated in vacuo, the residue was filtered over silica gel. The 4-hydroxy-6-methyl-4,5,6,7-tetrahydro-furano[2,3-c]pyridine hydrochloride (m.p.: 169°–170° C.) was obtained.

The compounds 2,6-dimethyl-4-hydroxy-furano[2,3-c]pyridine (melting point of the hydrochloride: 189°–190° C.) and 2-ethyl-4-hydroxy-6-methyl-furano[2,3-c]pyridine (melting point of the hydrochloride: 176°–178° C.) were also obtained in this way.

By use of procedures analogus to that described above, the following compounds were prepared:
Starting from 4-hydroxy-4,5,6,7-tetrahydro-furano[2,3-c]pyridine:
(i) 4-(o-hydroxyphenyl)-4,5,6,7-tetrahydro-furano[2,3-c]pyridine (m.p.: 186°–187° C.)
Starting from 2-methyl-4-hydroxy-4,5,6,7-tetrahydro-furano[2,3-c]pyridine:
(ii) 2-methyl-4-(p-methoxyphenyl)-4,5,6,7-tetrahydro-furano[2,3-c]pyridine (hydrochloride m.p.: 255°–256° C.)

The 4-hydroxy-4,5,6,7-tetrahydro-furano[2,3-c]pyridine used as starting compound was prepared in the following manner:

Thirty-six grams (0.17 mol) of 4-oxo-6-ethoxycarbonyl-4,5,6,7-tetrahydro-furano[2,3-c]pyridine were dissolved in 100 ml of ethanol and stirred with 10 gm (0.25 mol) of sodium borohydride for 30 minutes at 40°–50° C. The solvent was eliminated in vacuo, and the residue was combined with 200 ml of water and extracted with ether. After drying, the ether was distilled off.

The residue, 4-hydroxy-6-ethoxycarbonyl-4,5,6,7-tetrahydro-furano[2,3-c]pyridine, was dissolved in 500 ml of methanol, mixed with 44 gm of potassium hydroxide, and heated to 120° C. in an autoclave for 48 hours. After cooling, the solvent was distilled off in vacuo, and the residue was dissolved in methylene chloride and dried in magnesium sulfate. Then, the solid components were subjected to suction filtration and the solvent was distilled off. The residue was dissolved in ethanol. After addition of ethereal hydrochloric acid, the hydrochloride of the title compound crystallized out.
Yield: 22 gm (73.5% of theory)
M.p.: 167°–168° C.

The compound 2-methyl-4-hydroxy-4,5,6,7-tetrahydro-furano[2,3-c]pyridine hydrochloride (m.p.: 200°–201° C. (decomp.)) was obtained in similar fashion.

Example 2

4-(p-Bromophenyl)-2,6-dimethyl-4,5,6,7-tetrahydro-furano[2,3-c]pyridine

Six grams (0.03 mol) of 2,6-dimethyl-4-hydroxy-4,5,6,7-tetrahydro-furano[2,3-c]pyridine and 10 ml of bromobenzene were dissolved in 60 ml of methylene chloride, mixed with 9 gm of aluminum chloride, and stirred for 15 minutes. The reaction mixture was poured onto ice, made alkaline with sodium hydroxide solution, and extracted with ethylene chloride. The solvent was distilled off, and the residue was purified over silica gel [cyclohexane/ethyl acetate (3:1)] and separated. The hydrochloride of the title compound crystallized out of the residue of the first fraction after addition of ethereal hydrochloride acid solution.
Yield: 2.5 gm (24.7% of theory)
M.p.: 203°–204° C.

After addition of ethereal hydrochloric acid solution, the hydrochloride of 4-(o-bromophenyl)-2,6-dimethyl-4,5,6,7-tetrahydro-furano[2,3-c]pyridine crystallized out from the residue of the second fraction.
Yield: 5.0 gm (49.4% of theory)
M.p.: 252°–253° C.

By use of procedures analogous to that described above, the following compounds were prepared:
Starting from 4-hydroxy-6-methyl-4,5,6,7-tetrahydro-furano[2,3-c]pyridine:
(i) 4-(p-tolyl)-6-methyl-4,5,6,7-tetrahydro-furano[2,3-c]pyridine (maleate m.p.: 180°–181° C.)
(ii) 4-phenyl-6-methyl-4,5,6,7-tetrahydro-furano[2,3-c]pyridine (maleate m.p.: 174°–175° C.)
Starting from 2,6-dimethyl-4-hydroxy-4,5,6,7-tetrahydro-furano[2,3-c]pyridine:
(iii) 2,6-dimethyl-4-(o-bromophenyl)-4,5,6,7-tetrahydro-furano[2,3-c]pyridine (hydrochloride m.p.: 203°–204° C.)
(iv) 2,6-dimethyl-4-(p-chlorophenyl)-4,5,6,7-tetrahydro-furano[2,3-c]pyridine (hydrochloride m.p.: 241°–242° C.)
(v) 2,6-dimethyl-4-(o-chlorophenyl)-4,5,6,7-tetrahydro-furano[2,3-c]pyridine (hydrochloride m.p.: 223°–224° C.)
(vi) 2,6-dimethyl-4-(p-fluorophenyl)-4,5,6,7-tetrahydro-furano[2,3-c]pyridine (hydrochloride m.p.: 209°–210° C.

(vii) 2,6-dimethyl-4-(o-fluorophenyl)-4,5,6,7-tetrahydro-furano[2,3-c]pyridine (hydrochloride m.p.: 242°–243° C.)

Starting from 4-hydroxy-4,5,6,7-tetrahydro-furano[2,3-c]pyridine:

(viii) 4-(p-fluorophenyl)-4,5,6,7-tetrahydro-furano[2,3-c]pyridine (maleate m.p.: 128°–129° C.)

Starting from 2-methyl-4-hydroxy-4,5,6,7-tetrahydro-furano[2,3-c]pyridine:

(ix) 2-methyl-4-(p-bromophenyl)-4,5,6,7-tetrahydro-furano[2,3-c]pyridine (hydrochloride m.p.: 273°–274° C.)

(x) 2-methyl-4-(o-bromophenyl)-4,5,6,7-tetrahydro-furano[2,3-c]pyridine (hydrochloride m.p.: 229°–230° C.)

(xi) 2-pyrrolidinomethyl-4-(p-methoxyphenyl)-6-methyl-4,5,6,7-tetrahydro-furano[2,3-c]pyridine (hydrochloride m.p.: 184°–185° C. (decomp.))

Starting from 2-methyl-4-hydroxy-6-ethyl-4,5,6,7-tetrahydro-furano[2,3-c]pyridine:

(xii) 2-methyl-4-phenyl-6-ethyl-4,5,6,7-tetrahydro-furano[2,3-c]pyridine (hydrochloride m.p.: 185°–186° C. (decomp.))

Starting from 2-methyl-4-hydroxy-6-n-propyl-4,5,6,7-tetrahydro-furano[2,3-c]pyridine:

(xiii) 2-methyl-4-phenyl-6-n-propyl-4,5,6,7-tetrahydro-furano[2,3-c]pyridine (oxalate m.p.: 166°–168° C.)

Starting from 2-methyl-4-hydroxy-6-n-butyl-4,5,6,7-tetrahydro-furano[2,3-c]pyridine:

(xiv) 2-methyl-4-phenyl-6-n-butyl-4,5,6,7-tetrahydro-furano[2,3-c]pyridine (oxalate m.p.: 114°–115° C.)

The starting compound 2-methyl-4-hydroxy-6-butyl-4,5,6,7-tetrahydro-furano[2,3-c]pyridine was obtained in the following manner:

Three grams (0.02 mol) of 2-methyl-4-hydroxy-4,5,6,7-tetrahydro-furano[2,3-c]pyridine were dissolved in 50 ml of ethanol, mixed with 3 ml of triethylamine and 3 gm of n-butylbromide, and refluxed for two hours. The reaction was largely evaporated in vacuo and mixed with water. The aqueous solution was extracted with ether. The ether was distilled off, and the title compound remained as a light yellow oil.

Yield: 2.6 gm (63.4% of theory)

M.p. of the hydrochloride: 165°–166° C.

The compounds 2-methyl-4-hydroxy-6-ethyl-4,5,6,7-tetrahydro-furano[2,3-c]pyridine (m.p. of the hydrochloride: 179°–180° C.) and 2-methyl-4-hydroxy-6-n-propyl-4,5,6,7-tetrahydro-furano[2,3-c]pyridine (m.p. of the hydrochloride: 170°–171° C.) were obtained in analogous fashion.

Example 3

4-(3,4-Dihydroxyphenyl)-4,5,6,7-tetrahydro-furano[2,3-c]pyridine

Sixteen grams of o-chlorobenzylchloride were added to a solution of 13 gm of 4-hydroxy-4,5,6,7-tetrahydro-furano[2,3-c]pyridine and 22 gm of triethylamine in 200 ml of ethanol, and the mixture was refluxed for one hour. The volatile fractions were largely eliminated in vacuo, and the residue was mixed with water. The solution was extracted with ether and dried. After the solvent was distilled off, 23 gm of light yellow oil, 4-hydroxy-6-(o-chlorobenzyl)-4,5,6,7-tetrahydrofurano[2,3-c]pyridine, remained, which was dissolved in 200 ml of methylene chloride and added dropwise to a solution of 14 gm of pyrocatechol and 100 ml of methane sulfonic acid in 200 ml of methylene chloride. After 30 minutes, the mixture was poured onto ice and neutralized with concentrated ammonia. The organic phase was separated off and dried. After the solvent was distilled off, the 4-(3,4-dihydroxyphenyl-6-(chlorobenzyl)-4,5,6,7-tetrahydro-furano[2,3-c]pyridine crystallized out (16 gm).

Debenzylation was carried out in methanol at ambient temperature under 5 bar with palladium/charcoal. After the catalyst was removed by suction filtration and the solvent was distilled off, the residue crystallized after the addition of ethereal hydrochloric acid.

Yield: 9 gm (77% of theory)

M.p.: 243°–244° C. (decomp.; from isopropanol).

By use of analogous procedures, hydrochlorides of the following compounds were prepared:

(i) 2-methyl-4-(3,4-dihydroxyphenyl)-4,5,6,7-tetrahydro-furano[2,3-c]pyridine (m.p.: 214°–215° C. (decompl)

(ii) 2-methyl-4-(1,4-benzodioxanyl)-4,5,6,7-tetrahydro-furano[2,3-c]pyridine (m.p.: 241°–242° C. (decomp.)).

Example 4

4-(p-Methoxyphenyl)-6-methyl-2-pyrrolidinomethyl-4,5,6,7-tetrahydro-furano[2,3-c]pyridine Two grams (0.00825 mol) of 4-(p-methoxyphenyl)-6-methyl-4,5,6,7-tetrahydro-furano[2,3-c]pyridine and 1.5 gm of methylene pyrrolidinium chloride were dissolved in 30 ml of absolute acetonitrile and heated to boiling for 30 minutes. When the solvent was distilled off in vacuo, the hydrochloride of the title compound precipitated.

Yield: 1.6 pm (52% of theory)

M.p.: 184°–185° C. (decomp.; from isopropanol).

Example 5

2-Methyl-4-p-acetyloxyphenyl-6-methyl-4,5,6,7-tetrahydro-furano[2,3-c]pyridine

A quantity of 2.5 gm (0.008 mol) of 2,6-dimethyl-4-(p-hydroxyphenyl)-4,5,6,7-tetrahydro-furano[2,3-c]pyridine was heated in 25 ml of acetic anhydride for 30 minutes to 100° C. The mixture was then neutralized with ammonia and extracted with ethyl acetate. The organic phase was dried, and the solvent was distilled off in vacuo. The hydrochloride of the title compound was crystallized out by the addition of ethereal hydrochloric acid to the residue.

Yield: 2.8 gm (88% of theory)

M.p.: 210°–211° C.

Example 6

2,6-Dimethyl-4-p-tolyl-4-hydroxy-4,5,6,7-tetrahydro-furano[2,3-c]pyridine

At −10° C., a solution of 1.5 gm (0.009 mol) of 2,6-dimethyl-4-oxo-4,5,6,7-tetrahydro-furano[2,3-c]pyridine in 10 ml of absolute tetrahydrofuran was added dropwise to a solution of 0.03 mol of p-tolyl magnesium bromide in 25 ml of absolute tetrahydrofuran. After the reaction, the mixture was poured onto ice and extracted with ether. After drying, the ether was distilled off, and the residue was dissolved in ethanol. Subsequent to addition of ethereal hydrochloric acid, the hydrochloride of the title compound crystallized out.

Yield: 2.3 gm (86% of theory)

M.p.: 180°–181° C. (from ethanol).

By use of procedures analogous to that described above, hydrochlorides of the following compounds were prepared:

Starting from 2,6-dimethyl-4-oxo-4,5,6,7-tetrahydro-furano[2,3-c]pyridine:
(i) 2,6-dimethyl-4-hydroxy-4-(p-bromophenyl)-4,5,6,7-tetrahydro-furano[2,3-c]pyridine (m.p.: 196°–197° C. (decomp.))
(ii) 2,6-dimethyl-4-hydroxy-4-(m-methoxyphenyl)-4,5,6,7-tetrahydro-furano[2,3-c]pyridine (m.p.: 173°–174° C. (decomp.))
(iii) 2,6-dimethyl-4-hydroxy-4-(p-ethylphenyl)-4,5,6,7-tetrahydro-furano[2,3-c]pyridine (m.p.: 181°–182° C.)
(iv) 2,6-dimethyl-4-hydroxy-4-(p-chlorophenyl)-4,5,6,7-tetrahydro-furano[2,3-c]pyridine (m.p.: 199°–200° C.).

The starting compound, 2,6-dimethyl-4-oxo-4,5,6,7-tetrahydro-furano[2,3-c]pyridine, was obtained as follows:

A quantity of 22.8 gm of aluminum isopropoxide in 500 ml of toluene was added dropwise to a solution of 10 gm (0.05 mol) of 2,6-dimethyl-4-hydroxy-4,5,6,7-tetrahydro-furano[2,3-c]pyridine and 100 ml of cyclohexanone in 1 liter of absolute toluene. The reaction mixture was refluxed for two hours. After cooling, 200 ml of 40% diammonium tartrate solution were added. The organic phase was separated off and dried. After the solvent was distilled off, the title compound remained as a yellow oil.
Yield: 5.5 gm (66.6% of theory)
M.p. of the hydrochloride: 222°–223° C.

In an analogous procedure, 4-oxo-4,5,6,7-tetrahydro-furano[2,3-c]pyridine (m.p. of the hydrochloride 243°–244° C.) was obtained from 4-hydroxy-6-methyl-4,5,6,7-tetrahydro-furano[2,3-c]pyridine. Also, starting from 4-oxo-6-methyl-4,5,6,7-tetrahydro-furano[2,3-c]pyridine, 4-hydroxy-4-(p-bromophenyl)-6-methyl-4,5,6,7-tetrahydro-furano[2,3-c]pyridine (hydrochloride m.p.: 212°–213° C. (decomp.)) was prepared.

Example 7

4-Methoxy-4-p-bromophenyl-6-methyl-4,5,6,7-tetrahydro-furano[2,3-c]pyridine

Two grams (0.005 mol) of 4-hydroxy-4-(p-bromophenyl)-6-methyl-4,5,6,7-tetrahydro-furano[2,3-c]pyridine were heated to 50° C. for four hours in 40 ml of a boron trifluoride/methanol mixture (20% $BF_3$), and then the mixture was poured onto ice and neutralized with ammonia. The mixture was extracted with ether, and the ether was distilled off in vacuo. The residue was purified over silica gel [cyclohexane/ethyl acetate (75:25)].
Yield: 1 gm (56% of theory)
M.p.: 151°–152° C. (decomp.).

Example 8

2-Hydroxymethyl-4-p-tolyl-6-methyl-4,5,6,7-tetrahydro-furano[2,3-c]pyridine

At 15° C., 1.2 gm (0.0041 mol) of 2-carbethoxy-4-p-tolyl-6-methyl-4,5,6,7-tetrahydro-furano[2,3-c]pyridine, dissolved in 10 ml of tetrahydrofuran, were added dropwise to 200 mg of lithium alanate in 10 ml of absolute tetrahydrofuran. The mixture was stirred at ambient temperature for 30 minutes. The excess lithium alanate was mixed with aqueous tetrahydrofuran. Then, 20 ml of 40% diammonium tartrate solution were added to the reaction mixture. The organic phase was separated off and dried. The solvent was distilled off in vacuo. The residue was filtered over silica gel [cyclohexane/ethyl acetate (1:3)]. After addition of alcoholic maleic acid, the maleate of the title compound crystallized out.
Yield: 1.1 gm (71% of theory)
M.p.: 94°–95° C.

In analogous manner, starting from 2-carbethoxy-4-p-tolyl-4-hydroxy-4,5,6,7-tetrahydro-furano[2,3-c]pyridine, the compound 2-hydroxymethyl-4-p-tolyl-4-hydroxy-4,5,6,7-tetrahydro-furano[2,3-c]pyridine maleate (m.p.: 156°–157° C.) was prepared by lithium alanate reduction.

The starting compound was obtained as follows:

(a)
2-Carbethoxy-4-oxo-6-benzyl-4,5,6,7-tetrahydro-furano[2,3-c]pyridine

One hundred ten grams (0.5 mol) of N-benzylpiperidine-3,5-dione and 32.5 g of potassium hydroxide were dissolved in 800 ml of ethanol. Seventy grams (0.51 mol) of chloroformyl acetic acid ester were added to this solution, and the resulting mixture was stirred for ten hours at ambient temperature. The solvent was largely distilled off in vacuo, and the residue was mixed with water. The reaction mixture was extracted with 1 liter of methylene chloride and dried. Under cooling with ice, 150 ml of methanesulfonic acid and 50 ml of methane sulfonic acid chloride were added dropwise to this solution, which was then stirred for four hours at ambient temperature. Next, the reaction mixture was poured onto ice and neutralized with concentrated ammonia. The organic phase was separated off and dried. After the solvent was distilled off, the residue was dissolved in a small amount of acetone. After the addition of ethereal hydrochloric acid, the hydrochloride of the title compound crystallized out.
Yield: 55 gm (40% of theory)
M.p.: 175°–176° C. (from ethanol)

(b)
2-Carbethoxy-4-p-tolyl-4-hydroxy-4,5,6,7-tetrahydro-furano[2,3-c]pyridine A quantity of 0.1 mol of 4-methyl-phenylmagnesium bromide in 60 ml of absolute tetrahydrofuran was added dropwise, under cooling with ice, to a solution of 15 gm (0.045 mol) of 2-carbethoxy-4-oxo-6-benzyl-4,5,6,7-tetrahydro-furano[2,3-c]pyridine in 60 ml of tetrahydrofuran, and the mixture was stirred for 30 minutes at 10° C. The reaction mixture was poured onto ice. After the addition of 50 ml of 2N hydrochloric acid, the hydrochloride of the N-benzyl derivative of the title compound crystallized out. (14.5 gm; m.p.: 194°–196° C.).

Debenzylation was carried out in 140 ml of ethanol at 30° C. under 5 bar with palladium/charcoal. After the catalyst was removed by suction filtration, the solvent was distilled off in vacuo. The title compound crystallized in ether.
Yield: 7.6 gm (75% of theory)
M.p.: 160°–161° C.

(c)
2-Carbethoxy-4-p-tolyl-6-methyl-4,5,6,7-tetrahydro-furano[2,3-c]pyridine An amount of 3.7 gm of (0.0123 mol) of 2-carbethoxy-4-p-tolyl-4-hydroxy-4,5,6,7-tetrahydro-furano[2,3-c]pyridine was dissolved in 40 ml of ethylene chloride, slowly mixed with 4 ml of thionyl chloride, and then stirred for 30 minutes at ambient temperature. The volatile fractions were distilled off in vacuo, and the residue was mixed with ice and neutralized with ammonia. The aqueous phase was extracted with methylene chloride, and the organic phase was dried and concentrated by evaporation in vacuo. After addition of isopropylether to the residue, 3 gm (84.5%) of 2-carbethoxy-4-p-tolyl-furano[2,3-c]pyridine crystallized out (m.p.: 116°–117° C.). This was dissolved in 28 ml of tetrahydrofuran and refluxed for six hours with 5 gm of sodium carbonate and 10 gm of methyl iodide. After cooling, methylene chloride and water were added until the organic phase separated. The organic phase was removed, dried, and concentrated in vacuo. The methyl pyridinium iodide (2.8 gm) was precipitated in the form of crystals, which were washed with ether (m.p.: 214°–215° C. (decomp)).

The pyridinium iodide formed was dissolved in 70 ml of ethanol and hydrogenated at 70° C., platinum oxide being used as catalyst. After the catalyst was removed by suction filtration, the residue was made alkaline with ammonia and extracted with methylene chloride. After the solvent was distilled off, the title compound remained as a light yellow oil.

Yield: 1.2 gm (66.5% of theory, based upon the methyl pyridinium iodide).

Example 9

4-p-Tolyl-6-methyl-4,5,6,7-tetrahydro-furano[3,2-c]pyridine

Twenty grams (0.08 mol) of 2-furfuryl-2-methyl-amino-1-p-methyl-phenyl-ethanol were dissolved in 100 ml of ethylene chloride and heated to boiling point for three hours with 100 ml of trifluoroacetic acid. The reaction mixture was poured onto ice and neutralized with concentrated ammonia. The organic constituents were extracted with ether. Aftery drying, the ether was distilled off in vacuo. The residue was purified over silica gel [cyclohexane/ethyl acetate (1:1)]. After the solvent was distilled off in vacuo, the residue was dissolved in acetate. After addition of ethereal hydrochloric acid, the hydrochloride of the title compound crystallized out.

Yield: 4.5 gm (19% of theory)
M.p.: 248°–249° C.

By use of procedures analogous to that described above, the following compounds were prepared:

(i) 4-phenyl-4,5,6,7-tetrahydro-furano[3,2-c]pyridine (m.p.: 237°–238° C. (hydrochloride))
(ii) 2,6-dimethyl-4-phenyl-4,5,6,7-tetrahydro-furano[3,2-c]pyridine (m.p.: 188°–189° C. (hydrochloride))
(iii) 4-(p-tolyl)-6-methyl-4,5,6,7-tetrahydro-furano[3,2-c]pyridine (m.p.: 248°–249° C. (hydrochloride))
(iv) 4-phenyl-6-methyl-4,5,6,7-tetrahydro-furano[3,2-c]pyridine (m.p.: 237°–238° C. (hydrochloride))
(v) 4-(p-bromophenyl)-6-methyl-4,5,6,7-tetrahydro-furano[3,2-c]pyridine (m.p.: 259°–260° C. (hydrochloride))
(vi) 4-(p-fluorophenyl)-6-methyl-4,5,6,7-tetrahydro-furano[3,2-c]pyridine (m.p.: 224°–225° C. (hydrochloride))
(vii) 4-(p-chlorophenyl)-6-methyl-4,5,6,7-tetrahydro-furano[3,2-c]pyridine (m.p.: 239°–240° C. (hydrochloride))
(viii) 2,6-dimethyl-4-(p-fluorophenyl)-4,5,6,7-tetrahydro-furano[3,2-c]pyridine (m.p.: 202°–203° C. (hydrochloride))
(ix) 4-(p-methoxyphenyl)-6-methyl-4,5,6,7-tetrahydro-furano[3,2-c]pyridine (m.p.: 221°–222° C. (hydrochloride))
(x) 2,6-dimethyl-4-(p-tolyl)-4,5,6,7-tetrahydro-furano[3,2-c]pyridine (m.p.: 224°–225° C. (hydrochloride))
(xi) 2,6-dimethyl-4-(p-chlorophenyl)-4,5,6,7-tetrahydro-furano[3,2-c]pyridine (m.p.: 177°–178° C. (hydrochloride))
(xii) 2,6-dimethyl-4-(p-bromophenyl)-4,5,6,7-tetrahydro-furano[3,2-c]pyridine (m.p.: 174°–175° C. (hydrochloride))
(xiii) 2,6-dimethyl-4-(p-methoxyphenyl)-4,5,6,7-tetrahydro-furano[3,2-c]pyridine (m.p.: 240°–241° C. (hydrochloride))
(xiv) 2-ethyl-4-(p-fluorophenyl)-6-methyl-4,5,6,7-tetrahydro-furano[3,2-c]pyridine (m.p.: 214°–215° C. (hydrochloride))
(xv) 2-methyl-4-phenyl-4,5,6,7-tetrahydro-furano[3,2-c]pyridine (m.p.: 284°–286° C. (decomp.; hydrochloride))
(xvi) 4-(3,4-dihydroxyphenyl)-4,5,6,7-tetrahydro-furano[3,2-c]pyridine (m.p.: 254°–255° C. (hydrochloride))
(xvii) 4-(3-hydroxyphenyl)-6-methyl-4,5,6,7-tetrahydro-furano[3,2-c]pyridine (m.p.: 251°–252° C. (hydrochloride))

The starting compound 2-furfuryl-2-methylamino-1-p-methylphenyl ethanol was obtained in the following manner:

A solution of 10 gm (0.082 mol) of furfurylmethylamine in 50 ml of ethanol and 10 gm of triethylamine was mixed with 17 gm of p-methylphenacylbromide and stirred for two hours. The triethylamine hydrochloride precipitated was subjected to suction filtration. The mother liquor was mixed with 4 gm of sodium borohydride and stirred for one hour at ambient temperature. Then, water was added, and the mixture was extracted with ether. The ether solution was dried, and the ether was distilled off in vacuo. The 2-furfuryl-2-methylamino-1-p-methylphenyl ethanol was left behind in the form of an oil.

(Yield: 20 gm (99% of theory).

FORMULATION EXAMPLES

Example 10

Coated Tablets

Each tablet core has the following composition:

| Component | Amount (mg) |
| --- | --- |
| Active substance according to the invention | 25.0 |
| Lactose | 50.0 |
| Corn starch | 22.0 |
| Gelatine | 2.0 |
| Magnesium stearate | 1.0 |
| TOTAL: | 100.0 |

Preparation

A mixture of the active substance with lactose and corn starch is granulated with a 10% aqueous gelatine solution by passing through a screen with a 1 mm mesh, drying at 40° C., and again passing through a screen. The granulate thus obtained is mixed with magnesium stearate and compressed. The resulting cores are coated in the usual manner with a coating applied by means of an aqueous suspension of sugar, titanium dioxide, talc, and gum arabic. The finished coated tablets are polished with beeswax.

Example 11

Tablets

Each tablet has the following composition:

| Component | Amount (mg) |
|---|---|
| Active substance according to the invention | 10.0 |
| Lactose | 40.0 |
| Corn starch | 44.0 |
| Soluble starch | 5.0 |
| Magnesium stearate | 1.0 |
| TOTAL: | 100.0 |

Preparation

The active substance and magnesium stearate are granulated with an aqueous solution of the soluble starch, and the granulate is dried and intimately mixed with lactose and corn starch. The mixture is then compressed to form tablets weighing 100 mg, each containing 10 mg of active substance.

Example 12

Suppositories

Each suppository has the following composition:

| Component | Amount (mg) |
|---|---|
| Active substance according to the invention | 10.0 |
| Suppository mass (e.g., WITEPSOL ® W 45, available from Chemische Werke Witten GmbH) | 1690.0 |
| TOTAL: | 1700.0 |

Preparation

Finely powdered substance is stirred into molten suppository mass, which has been cooled to 40° C., an immersion homogenizer being used. The mass is poured at 35° C. into slightly chilled molds.

Example 13

Ampules (Injection Solutions)

Each ampule has the following composition:

| Component | Amount (parts by weight) |
|---|---|
| Active substance according to the invention | 5.0 |
| Sodium pyrosulfite | 1.0 |
| Disodium salt of ethylenediaminetetraacetic acid | 0.5 |
| Sodium chloride | 8.5 |
| Twice distilled water ad | 1,000.0 |

Preparation

The active substance and excipients are dissolved in sufficient water and brought to the desired concentration with the required quantity of water. The solution is filtered and, under aseptic conditions, transferred into 1 ml ampules. Finally, the ampules are sterilized and sealed. Each ampule contains 5.0 mg of active substance.

Any of the other compounds embraced by Formula I or II, or a combination thereof, may be employed as the particular active ingredient employed in Examples 10 through 13. Likewise, the amount of active ingredient in these illustrative examples may be varied to achieve the dosage unit range set forth above, and the amounts and nature of the inert pharmaceutical carrier ingredient may be varied to meet particular requirements.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

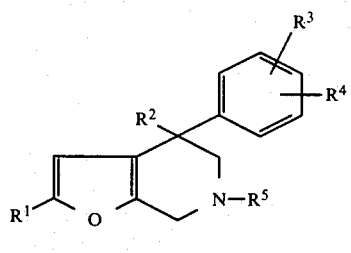

or

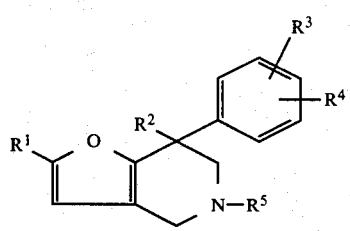

wherein
$R^1$ represents hydrogen, fluorine, chlorine, bromine, an alkyl group having from 1 to 4 carbon atoms, a hydroxyalkyl group having 1 or 2 carbon atoms, an alkoxyalkyl group wherein each alkyl group may have 1 or 2 carbon atoms, a pyrrolidinomethyl group, or a dialkylaminomethyl group wherein each alkyl group may have 1 or 2 carbon atoms;
$R^2$ represents hydrogen, hydroxyl, methoxy, or ethoxy;
$R^3$ and $R^4$, which may be the same or different, each represent hydrogen, fluorine, chlorine, bromine, methyl, ethyl, hydroxyl, methoxy, acetoxy, or benzyloxy or $R^3$ and $R^4$ together with the phenyl ring form a 3,4-benzodioxanyl group;
$R^5$ represents hydrogen, an alkyl group having from 1 to 4 carbon atoms, or a benzyl or o-chlorobenzyl group,
with the proviso that in Formula II $R^2$ represents hydrogen and $R^1$ does not represent hydroxyalkyl, or a pharmaceutically acceptable acid addition salt thereof.

2. A compound of claim 1, wherein in Formula I
$R^1$ represents hydrogen or a methyl group;
$R^2$ represents hydrogen or a hydroxyl group;
$R^3$ and $R^4$, which may be the same or different, each represent hydrogen, hydroxyl, or bromine or together with the phenyl ring represent the benzodioxanyl group; and
$R^5$ represents hydrogen or a methyl group,
or a pharmacologically acceptable acid addition salt thereof.

3. A compound of claim 1, wherein in Formula II
$R^1$ represents hydrogen or a methyl group;

$R^2$ represents hydrogen;

$R^3$ and $R^4$, which may be the same or different, each represent hydrogen, hydroxyl, or bromine or, together with the phenyl ring, represent the benzodioxanyl group; and $R^5$ represents hydrogen or a methyl group, or a pharmacologically acceptable acid addition salt thereof.

4. The compound of claim 1 which is 2,6-dimethyl-4-hydroxy-4-p-bromophenyl-4,5,6,7-tetrahydro-furano[2,3-c]pyridine or a pharmacologically acceptable acid addition salt thereof.

5. The compound of claim 1 which is 2,6-dimethyl-4-(3,4-dihydroxyphenyl)-4,5,6,7-tetrahydro-furano[2,3-c]pyridine or a pharmacologically acceptable acid addition salt thereof.

6. The compound of claim 1 which is 4-(3,4-dihyroxyphenyl-4,5,6,7-tetrahydro-furano[2,3-c]pyridine or a pharmacologically acceptable acid addition salt thereof.

7. The compound of claim 1 which is 4-(3,4-dihydroxyphenyl)-6-methyl-4,5,6,7-tetrahyro-furano[2,3-c]pyridine or a pharmacologically acceptable acid addition salt thereof.

8. The compound of claim 1 which is 2-methyl-4-benzodioxanyl-4,5,6,7-tetrahydro-furano[2,3-c]pyridine or a pharmacologically acceptable salt thereof.

9. A pharmaceutical composition comprising as active substance an anti-depressively effective amount of one or more compounds of claim 1 in conjunction with conventional excipients and/or carriers.

10. A method of treating depressive states of various origins which comprises administering to a warm-blooded host in need of such treatment an anti-depressively effective amount of one or more compounds of claim 1 in conjunction with conventional excipients and/or carriers.

* * * * *